US006661580B1

United States Patent
Solarz

(10) Patent No.: US 6,661,580 B1
(45) Date of Patent: Dec. 9, 2003

(54) HIGH TRANSMISSION OPTICAL INSPECTION TOOLS

(75) Inventor: Richard William Solarz, Danville, CA (US)

(73) Assignee: KLA-Tencor Technologies Corporation, Milpitas, CA (US)

(*) Notice: Subject to any disclaimer, the term of this patent is extended or adjusted under 35 U.S.C. 154(b) by 0 days.

(21) Appl. No.: 10/187,005

(22) Filed: Jun. 28, 2002

Related U.S. Application Data

(63) Continuation-in-part of application No. 10/072,469, filed on Feb. 6, 2002, which is a continuation of application No. 09/602,920, filed on Jun. 23, 2000, now Pat. No. 6,362,923.
(60) Provisional application No. 60/188,309, filed on Mar. 10, 2000.

(51) Int. Cl.[7] .............................. G02B 7/00; G02B 5/08; G02B 17/00; G02B 21/06
(52) U.S. Cl. ..................... 359/642; 359/351; 359/355; 359/365; 359/385; 359/566; 359/823; 355/53; 355/67; 356/237.4; 250/492.2
(58) Field of Search ................................ 359/350, 351, 359/355, 364, 365, 385, 558, 566, 619, 622, 642, 823; 356/237.1, 237.2, 237.4; 250/492.2; 355/43, 53, 67; 430/30

(56) References Cited

U.S. PATENT DOCUMENTS

| | | | | | |
|---|---|---|---|---|---|
| 5,999,310 | A | * | 12/1999 | Shafer et al. | 359/351 |
| 6,115,175 | A | * | 9/2000 | Maruyama et al. | 359/355 |
| 6,320,697 | B2 | * | 11/2001 | Takeuchi | 359/385 |
| 6,483,638 | B1 | * | 11/2002 | Shafer et al. | 359/351 |
| 6,486,940 | B1 | * | 11/2002 | Williamson | 355/67 |
| 6,512,631 | B2 | * | 1/2003 | Shafer et al. | 359/355 |

* cited by examiner

Primary Examiner—Loha Ben
(74) Attorney, Agent, or Firm—Beyer Weaver & Thomas, LLP

(57) ABSTRACT

Techniques for increasing the percentage of light that is transmitted through optical inspection systems that operate in or near the ultraviolet and deep ultraviolet electromagnetic spectrums are described. Along with increasing the amount of light transmission, the techniques of the present invention also provide additional advantages such as reduction of ripple, increased ability to match inspection systems, and improving manufacturability. The techniques of the present invention involve using an auto-focus light source near the operational range of the inspection system and slightly raising the lower end of the operational range.

32 Claims, 3 Drawing Sheets

US 6,661,580 B1

HIGH TRANSMISSION OPTICAL INSPECTION TOOLS

CROSS-REFERENCE TO RELATED APPLICATIONS

This application is a continuation-in-part of U.S. patent application Ser. No. 10/072,469, filed Feb. 6, 2002, entitled "MULTI-DETECTOR MICROSCOPIC INSPECTION SYSTEM," which is a continuation of U.S. patent application Ser. No. 09/602,920, filed Jun. 23, 2000, entitled "Lens For Microscopic Inspection," now U.S. Pat. No. 6,362,923, which claims priority of U.S. provisional patent application No. 60/188,309, filed Mar. 10, 2000, entitled "IMPROVED LENS FOR MICROSCOPIC INSPECTION," which are each hereby incorporated by reference.

FIELD OF THE INVENTION

The present invention relates generally to optical inspection systems, and more specifically to auto-focusing techniques for optical inspection systems.

BACKGROUND OF THE INVENTION

Generally, the industry of semiconductor manufacturing involves highly complex techniques for integrating circuits into semiconductor materials. Due to the large number of processing steps and the decreasing size of semiconductor devices, the semiconductor manufacturing process is prone to processing defects that decrease device yields. Testing procedures to eliminate these processing defects from the processing steps are therefore critical for maintaining high yielding production facilities. Since the testing procedures are an integral and significant part of the manufacturing process, the semiconductor industry constantly seeks more sensitive and efficient testing procedures.

FIG. 1 is a diagrammatic view of a typical optical semiconductor inspection system 100 that includes an integrated auto-focus mechanism 114. FIG. 1 illustrates only the components of an optical inspection system that are relevant to the description of the present invention, therefore various components necessary for operation of the inspection system are not shown. FIG. 1 shows an illumination source 102 that directs light or photons through one or more sets of optical lenses 104 so that a semiconductor wafer specimen 106 can be illuminated and inspected. Optical lens set 104 illustrated in FIG. 1 is an objective lens set. Photons reflected off of specimen 106 are directed back to an inspection detector 108 through beam splitter 110. Inspection detector 108 detects photons reflected off of specimen 106 for inspection purposes. In order for inspection system 100 to produce accurate inspection results, specimen 106 should be positioned within a very small depth of field 112. Otherwise, sensitivity of inspection system 100 will be lost.

To ensure that specimen 106 is within the depth of field 112, auto-focus mechanism 114 is used. Auto-focus mechanism 114 includes a light emitting diode (LED) 116 that directs an auto-focusing light beam 118 into optical lenses 104 such that light beam 118 hits specimen 106, then is directed back into auto-focusing detector 120 via beam splitters 122 and 124. Gratings 126 and 128, which are offset slightly from each other, are placed respectively in front of LED 116 and auto-focusing detector 120. Grating images 126(a) and 128(a) are shown to illustrate the their respective orientations. The position of specimen 106 with respect to field of view 112 affects the intensity of light detected at auto-focus detector 120. Therefore, the focus of optical system 100 can be monitored through auto-focus mechanism 114. Auto-focus device uses at least some of the same optical lens elements in the system as illumination source 102. FIG. 1 illustrates an embodiment where illumination source 102 and auto-focus device 114 both direct light beams through objective lens section 104. Specifically, auto-focus light beam 118 is directed through the field of view of objective lens section 104.

As is commonly known, anti-reflective coatings (AR coatings) are formed on the surfaces of the optical lenses of an optical inspection system. AR coatings beneficially reduce reflections off of the lens surfaces, however, they also tend to reduce the amount of light that can be transmitted through the lenses. As will be described in further detail below, these AR coatings also cause undesirable effects such as reducing the sensitivity of an optical inspection system.

BRIEF SUMMARY OF THE INVENTION

In general, the present invention pertains to techniques for increasing the percentage of light that is transmitted through optical inspection systems that operate in or near the ultraviolet and deep ultraviolet electromagnetic spectrums. Along with increasing the amount of light transmission, the techniques of the present invention also provide additional advantages such as reduction of ripple, increased ability to match inspection systems, and improving manufacturability. The techniques of the present invention involve using an auto-focus light source near the operational range of the inspection system and slightly raising the lower end of the operational range.

One aspect of the present invention pertains to a microscope optical inspection system that includes at least one set of inspection optical lens elements, an illumination source that directs light into the set of inspection optical lens elements, wherein the operational bandwidth of light used for inspection is approximately within the ultraviolet and deep ultraviolet range or within portions thereof, and an auto-focus device that directs an auto-focusing light beam into at least some of the set of inspection optical lens elements, wherein the wavelength of the auto-focusing light beam is proximate to or within the operational bandwidth.

Another aspect of the present invention pertains to a microscope optical inspection system that includes at least one set of inspection optical lens elements, an illumination source that directs light into the set of inspection optical lens elements, and an auto-focus device that directs an auto-focusing light beam into at least some of the set of inspection optical lens elements, wherein the auto-focus device uses a light emitting diode or semiconductor laser made of gallium and nitride.

These and other features and advantages of the present invention will be presented in more detail in the following specification of the invention and the accompanying figures, which illustrate by way of example the principles of the invention.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE INVENTION

Figure 2:
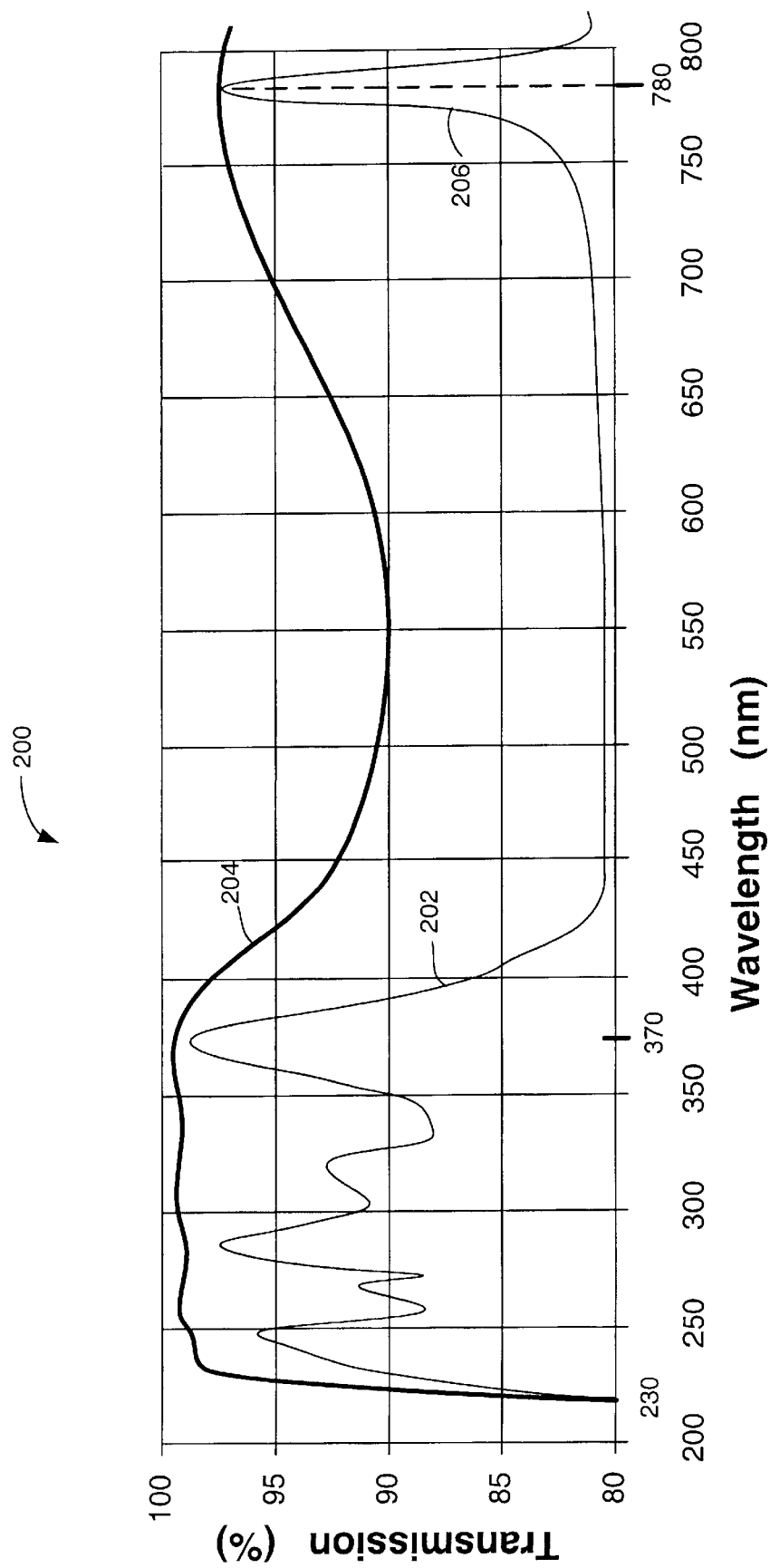
FIG. 2 shows a graph that illustrates the amount of illumination and auto-focus light that is transmitted through a current optical inspection system that operates in the region in and near the ultraviolet region.

For a better understanding of the present invention, a description of how current optical inspection systems operate will now be presented. Optical inspection systems utilize light or photons in a specific range of wavelengths to illuminate and inspect a specimen. This range of wavelengths is referred to as the operational range of an inspection system. For example, an optical inspection system operating in the ultraviolet and deep ultraviolet range typically uses illuminating light having wavelengths in approximately the range of 200–370 nanometers (nm). It should be appreciated that the upper and lower ends of this range of wavelengths varies can vary. These optical inspection systems also use an auto-focusing mechanism having a light emitting diode (LED) that emits light having much larger wavelengths. For example, a typical auto-focusing mechanisms use illumination sources made of gallium arsenide that emit light at approximately 780 nanometers. FIG. 2 shows a graph 200 that illustrates the amount of illumination and auto-focus light that is transmitted through a current optical inspection system that operates in the region in and near the ultraviolet region. Graph 200 is placed on a coordinate system in which the y-axis represents the percentage of transmitted light and the x-axis represents the wavelength of the light. Curve 202 represents the amount of light from both of the illumination and auto-focus sources that are transmitted through an inspection system. The portion of curve 202 in the range of approximately 230–370 nm represents the light from the illumination source that is transmitted through the system. The spike in curve 202 at approximately 780 nm represents the light from the auto-focus light source that is transmitted through the system. The auto-focus wavelength is designated with the dashed line 206. Note that very little light is transmitted through the system in the range of 370–780 nm.

As is typically required in optical inspection systems, the individual optical lenses are provided with multiple anti-reflective coatings (AR coatings). In order to allow for light transmission in the operational range of 230–370 nm and in the fairly separated auto-focus range of approximately 780 nm, a complex layering of multiple AR coatings is required on each optical lens surface. The resulting layering of AR coatings gives each optical lens a light transmission quality as represented by AR coating transmission curve 204. AR coating transmission curve 204 shows that the AR coatings for each lens surface transmit a large percentage of the illumination light (in the range of approximately 230–370 nm) and the auto-focus light (in the range of approximately 780 nm), however, 100% transmission is not typically observed. In between these two ranges, the AR coatings are designed to block or absorb light.

Given that a typical optical inspection system has many surfaces, the cumulative amount of light transmission through the system, which is the light transmission from the illumination lamp to the detector, is typically reduced to as low as 10%. In some systems, the cumulative light transmission can be even lower than 10%. It must be noted that wafer inspection tools need a strong enough signal at the detectors for statistical examination of the wafer images to detect the presence of defects. Unfortunately, the multiple AR coating layers reduce light transmission to the point that the speed and sensitivity of inspection systems can also be reduced, especially when operating in the ultraviolet and deep ultraviolet ranges. For instance, low levels of light provide for fewer levels of grayscale for imaging and detecting defects on a specimen. Also, to accumulate enough signal photons for the sensitivity required, the speed of scanning the wafer may be slowed down if enough light is not available. Therefore, increasing the illumination light transmission levels of an optical inspection system would increase the speed and resolution of optical inspection systems.

Additionally, the complex layers of AR coatings cause optical inspection systems to have inconsistent levels of transmission. This is particularly troublesome in the operational wavelength range. This is referred to as "ripple." Ripple is the statistical variation of the transmission of a batch of coatings from a given coating run as measured at various wavelengths within the bandwidth and is caused by normal variations in the optical layer thickness in multi-layer coatings. Ripple is evident in FIG. 2 where transmission curve 204 is shown to have a fluctuating amount of transmission in the range of approximately 230–370 nm. Ideally, transmission curve 204 would have a constant transmission level in this range. Typically, the broader the wavelength band that the AR coatings must operate over, the more layers are needed in the design and so the more likely it is to have process variations. Inspection systems that set the auto-focus wavelength at a far distance from the operational wavelength range, like the system represented in FIG. 2, therefore require many AR coating layers. In some embodiments of current systems, as many as twenty or more layers of AR coatings are required on each lens surface. This makes it very difficult to avoid ripple effects and to have high levels of transmission. As can be seen, curve 202 fluctuates in the operational range of approximately 230–370 nm. This fluctuation is in part due to the fluctuating transmissive qualities of the AR coatings. Obviously, this affects the sensitivity of the inspection tool at the various wavelengths. Additionally, the amount of light transmission decreases as the number of AR coatings used is increased.

The statistical variation that comes along with ripple makes it very difficult to achieve matching. Matching is the situation where two identical inspection systems are able to produce the same inspection results for an identical specimen. Ripple makes matching difficult because the AR coatings cause random variation in the amount of light transmission for inspection systems. This is undesirable as multiple optical inspection systems are less likely to produce the same inspection results for the same specimen. The ability to match tools provides for consistent recipe setup and portability of recipes.

Forming the multi-layer AR coatings is very difficult. Errors in forming an AR coating are usually non-reversible, thereby requiring lenses that have improperly formed AR coatings to be discarded. This difficulty is greatly increased as the number of coatings required increases. For systems that utilize light in the wavelengths as described in FIG. 2, up to 20 layers and more can be required for each lens surface. The AR coatings therefore greatly increase the difficulty and expense of manufacturing inspection systems.

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known operations have not been described in detail so not to unnecessarily obscure the present invention.

In general, the present invention pertains to techniques for increasing the percentage of light that is transmitted through optical inspection systems that operate in or near the ultraviolet and deep ultraviolet electromagnetic spectrums. The techniques of the present invention involve using an auto-focus light source near the operational range of the inspection system and slightly raising the lower end of the operational range.

Figure 3:
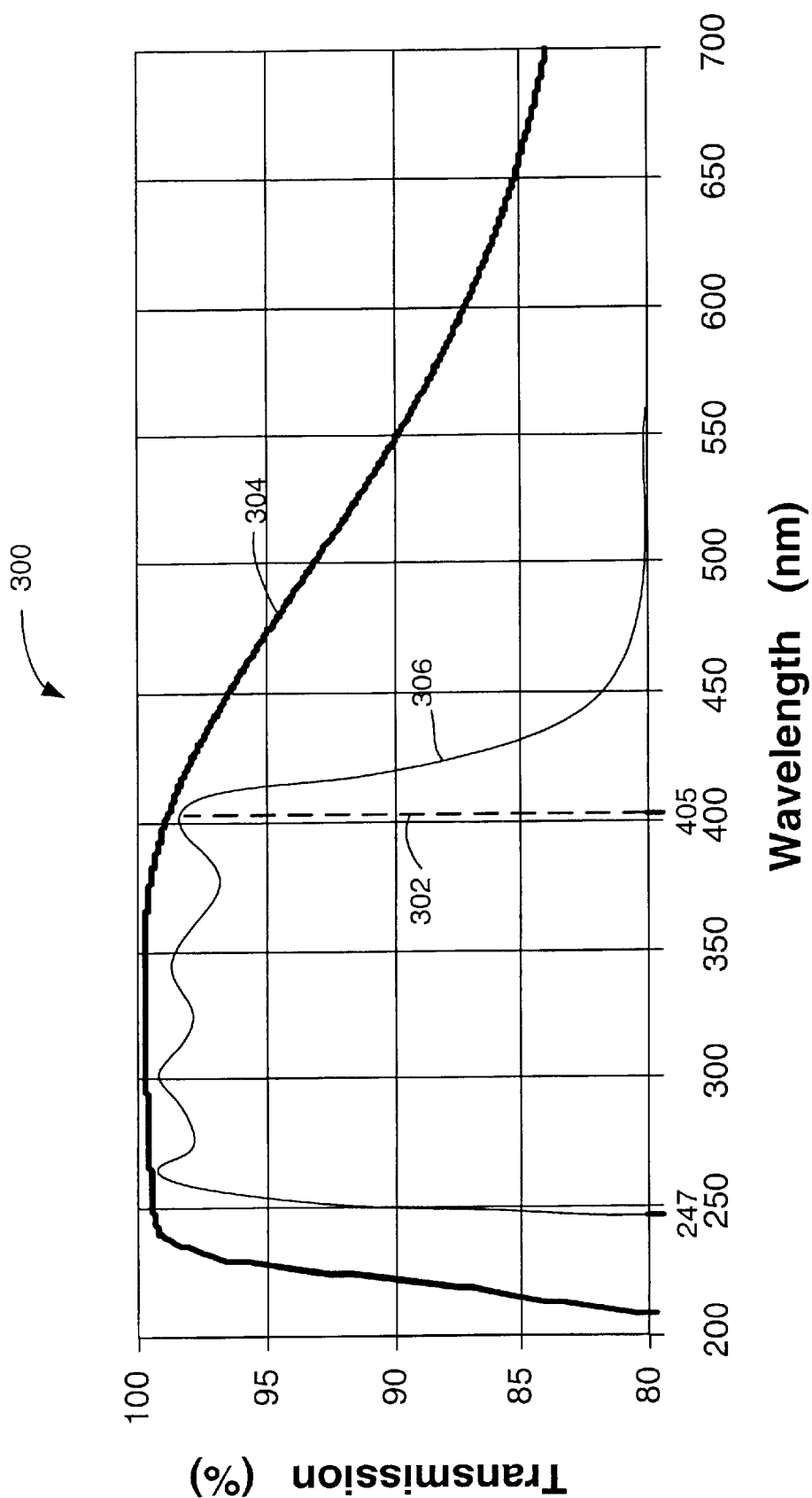
FIG. 3 illustrates a graph of the amount of illumination light and auto-focus light that is transmitted through an optical inspection system of the present invention.

FIG. 3 illustrates a graph 300 of the amount of illumination light and auto-focus light that is transmitted through an optical inspection system of the present invention. The y-axis of graph 300 represents the percentage of transmitted light and the x-axis represents the wavelength of light passing through the inspection system. The optical inspection system of the present invention operates in and near the spectral range of ultraviolet and deep ultraviolet light. For instance, the inspection system can operate in the wavelength ranges of approximately 190–450 nanometers. The operational range of the inspection system can vary among different embodiments of the invention. The inspection system uses a mercury-xenon illumination source. The illumination source can be a lamp, an excimer laser, a light emitting diode, a laser diode, or a harmonically converted solid-state laser.

This invention can be used with a catadioptric or non-catadioptric objective lens. This invention is operable for both illumination sources that emit a continuous bandwidth of light or a non-continuous bandwidth of light. An example of a non-continuous light source includes a light source having two or more separate lasers that emit light at different wavelengths. The inspection system can operate in either broad or narrow band modes.

Figure 1:
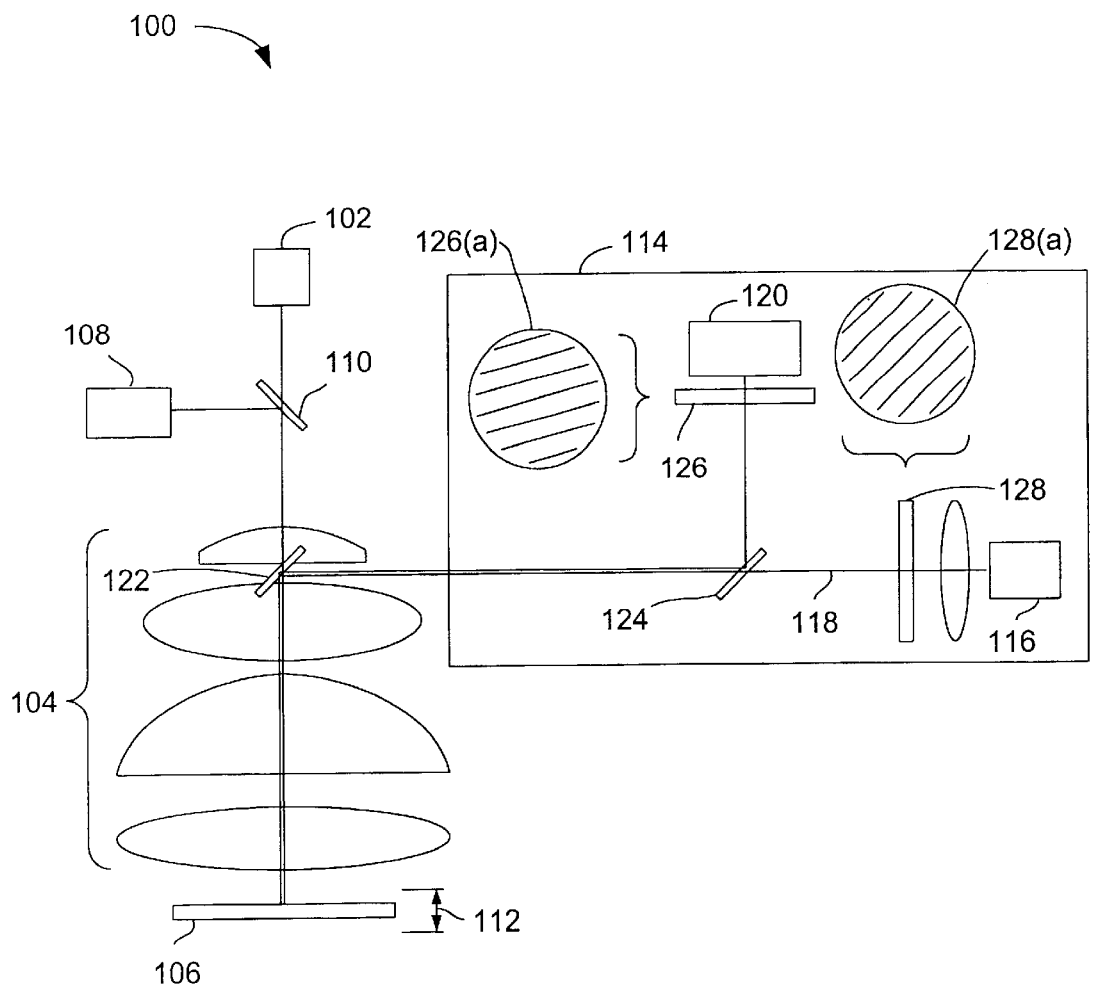
FIG. 1 is a diagrammatic view of a typical optical semiconductor inspection system that includes an integrated auto-focus mechanism.

Graph 300 illustrates the two main aspects of the present invention. First, the auto-focus wavelength 302 has been moved down to the violet range of the electromagnetic spectrum. In the embodiment of FIG. 3, the auto-focus wavelength is at approximately 405 nm. Dashed line 302 designates the auto-focus wavelength. Second, the AR coatings on the surfaces of the optical lenses are coated such that they efficiently transmit light photons of the mercury-xenon illumination source from approximately 247–500 nanometers. The AR coatings therefore narrow the operational bandwidth of the inspection tool. As described with respect to FIG. 1, the illumination light source and the auto-focus light source direct light through the same objective lens section of the inspection system.

With respect to the auto-focus wavelength, its wavelength of approximately 405 nm is much closer to the operational range in comparison to the system represented in FIG. 2. The auto-focus light source used to produce the light at 405 nm is formed of at least gallium (Ga) and nitrogen (N). The light source can be a variety of devices including but not limited to a light emitting diode, a semiconductor laser, and a frequency upconverted solid-state laser. In some embodiments the auto-focus light source also includes other materials. For instance, the auto-focus light source can also be made of indium-gallium-nitride or aluminum-gallium-nitride. In other embodiments, the auto-focus light source can made to emit light having wavelengths in the range of 300–500 nm. This range of wavelengths allows the auto-focus light to be proximate to or within the range of illumination light wavelengths. Since the operational photons and the auto-focus photons are closer together with respect to wavelengths, the AR coatings need to efficiently transmit light in a smaller range. Specifically, the system in FIG. 3 only needs to efficiently transmit light between 247 and 370 nm. Since the AR coatings need to be efficient in a smaller range, as compared to the AR coatings required for the system of FIG. 2, less complicated AR coatings are required. For instance, fewer layers of AR coatings are required. In turn, the simplified AR coatings allow for a larger percentage of light to be transmitted through the optical system.

In comparison to the inspection system represented in FIG. 2, the lower end of the operational range is raised from 230 nm to 247 nm. By raising the lower end of the operational bandwidth, illumination below approximately 247 nm is foregone, however the utility from the amount of light lost for illumination is more than compensated by the ability to narrow the operational bandwidth of the inspection system and therefore simplify the layers of AR coatings required. Raising the lower end of the operational band also permits the use of AR coating materials that absorb light photons having wavelengths below approximately 247 nm. Again, this allows for a greater amount of light to be transmitted through the optical system at wavelengths greater than approximately 247 nm. In some embodiments, the amount of illumination through the inspection system is doubled. Preferably, the coatings on the lens surfaces are formed to efficiently transmit light in the wavelength range of 247–370 nm. In some embodiments, the AR coatings on the lens surfaces efficiently transmit light in the wavelength range of approximately 247–370 nanometers. In alternative embodiments, the coatings can be adjusted to transmit light beyond this range, however, it should be understood that the amount of light transmitted through the optical system might be reduced.

Typically, twenty or more layers of AR coatings are required for an optical inspection system operating in the UV and deep UV spectral ranges. However, with the combination of the auto-focus light being moved closer to the operational range of the inspection system and with the narrowing of the transmissive range of the AR coatings, dramatically fewer AR coatings are required. In one embodiment, four AR coatings per optical lens surface are sufficient. Each of the AR coatings can be formed from a variety of materials including, but not limited to, $Sc_2O_3$, $HfO_2$, $ZrO_2$, and $Y_2O_3$. In some embodiments, each of the AR coating layers has a thickness in the range of approximately 25–250 nanometers.

As mentioned above, by placing the auto-focus light proximate to the operational range and slightly narrowing the operational bandwidth of the inspection system, the amount of light transmitted through the optical system is increase. This is beneficial because the additional light increases the resolution of the inspection system. However, the invention also produces additional advantages. Another beneficial effect of the invention is that fewer AR coating layers are required. This is both easier and less costly to manufacture. Also, the resulting AR coatings exhibit less ripple effect. In other words, the AR coatings transmit a more uniform level of light with respect to each of the various wavelengths at which light is transmitted. This is illustrated in FIG. 3 where curve 306 is shown to have less fluctuation in the degree of transmission in the range of approximately 247–350 nm. By reducing the ripple effect, it becomes much easier to manufacture multiple optical inspection systems that match each other.

The advantages of the invention are fully realized when both of the aspects of moving the auto-focus wavelength closer to the operational wavelength range and designing the AR coatings to efficiently transmit light in the range of approximately 247–370 nm are implemented. In some embodiments, one of the aspects can be implemented without the other even though the advantages are achieved to a lesser degree.

While this invention has been described in terms of several preferred embodiments, there are alteration, permutations, and equivalents, which fall within the scope of this invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

I claim:

1. A microscope optical inspection system comprising:
   at least one set of inspection optical lens elements;
   an illumination source that directs light into the set of inspection optical lens elements, wherein an operational bandwidth of light used for inspection is approximately within the ultraviolet and deep ultraviolet range or within portions thereof;
   an auto-focus device that directs an auto-focusing light beam into at least some of the set of inspection optical lens elements, wherein the wavelength of the auto-focusing light beam is proximate to or within the operational bandwidth.

2. A microscope optical inspection system as recited in claim 1 wherein the operational bandwidth of light includes light wavelengths in the range of approximately 190–450 nanometers, or portions thereof.

3. A microscope optical inspection system as recited in claim 1 wherein the illumination source is a mercury-xenon illumination source.

4. A microscope optical inspection system as recited in claim 3 wherein the mercury-xenon illumination source is a type selected from the group consisting of a lamp, an excimer laser, a light emitting diode, a laser diode, and a harmonically converted solid state laser.

5. A microscope optical inspection system as recited in claim 1 wherein the auto-focusing light beam is approximately in the range of 300 to 500 nanometers.

6. A microscope optical inspection system as recited in claim 5 wherein wavelength of the auto-focusing light beam is approximately 405 nanometers.

7. A microscope optical inspection system as recited in claim 5 wherein wavelength of the auto-focusing light beam is approximately 460 nanometers.

8. A microscope optical inspection system as recited in claim 5 wherein at least one of the optical lens elements has a layered formation of multiple anti-reflective coatings that transmit light wavelengths in the range of approximately 247–450 nanometers.

9. A microscope optical inspection system as recited in claim 5 wherein at least one of the optical lens elements has a layered formation of multiple anti-reflective coatings that transmit light wavelengths in the range of approximately 247–370 nanometers.

10. A microscope optical inspection system as recited in claim 8 wherein at least one of the anti-reflective coatings is formed of a material selected from the group consisting of $Sc_2O_3$, $HfO_2$, $ZrO_2$, and $Y_2O_3$.

11. A microscope optical inspection system as recited in claim 10 wherein an anti-reflective coating within a respective layered formation of anti-reflective coatings has a thickness in the range of approximately 25–250 nanometers.

12. A microscope optical inspection system as recited in claim 8 wherein the at least one optical lens element is part of an objective lens unit.

13. A microscope optical inspection system as recited in claim 1 wherein the auto-focusing light beam is produced by an auto-focus light source made of at least gallium and nitride.

14. A microscope optical inspection system as recited in claim 13 wherein the auto-focus light source is made of a composition selected from the group consisting of gallium-nitride, aluminum-gallium-nitride, and indium-gallium-nitride.

15. A microscope optical inspection system as recited in claim 13, wherein the auto-focus light source is a device selected from the group consisting of a light emitting diode, a semiconductor laser, and a frequency upconverted solid-state laser.

16. A microscope optical inspection system as recited in claim 1 wherein the optical inspection system is a catadioptric optical inspection system.

17. A microscope optical inspection system comprising:
    at least one set of inspection optical lens elements;
    an illumination source that directs light into the set of inspection optical lens elements;
    an auto-focus device that directs an auto-focusing light beam into at least some of the set of inspection optical lens elements, wherein the auto-focus device uses an auto-focusing light source made of at least gallium and nitride.

18. A microscope optical inspection system as recited in claim 17 wherein the auto-focusing light source is made of a composition selected from the group consisting of gallium-nitride, aluminum-gallium-nitride, and indium-gallium-nitride.

19. A microscope optical inspection system as recited in claim 17 wherein an operational bandwidth of light used for inspection is approximately within the range of approximately 190–450 nanometers, or portions thereof.

20. A microscope optical inspection system as recited in claim 17 wherein the illumination source is a mercury-xenon illumination source.

21. A microscope optical inspection system as recited in claim 17 wherein the wavelength of the auto-focusing light beam is proximate to or within the range of wavelengths of an operational bandwidth.

22. A microscope optical inspection system as recited in claim 17 wherein the auto-focusing light beam is approximately in the range of 300 to 500 nanometers.

23. A microscope optical inspection system as recited in claim 22 wherein wavelength of the auto-focusing light beam is approximately 405 nanometers.

24. A microscope optical inspection system as recited in claim 22 wherein wavelength of the auto-focusing light beam is approximately 460 nanometers.

25. A microscope optical inspection system comprising:
    at least one set of inspection optical lens elements;
    a layered formation of multiple anti-reflective coatings formed on each optical lens element wherein each layered formation is configured to transmit light wavelengths in the range of approximately 247–450 nanometers;
    an illumination source that directs light into the set of inspection optical lens elements, wherein the illumination source is a mercury-xenon lamp or laser and wherein an operational bandwidth of light used for inspection is approximately within the ultraviolet and deep ultraviolet range or within portions thereof;

an auto-focus device that directs an auto-focusing light beam into at least some of the set of inspection optical lens elements, wherein the auto-focus device uses an auto-focusing light source made of at least gallium and nitride and wherein the wavelength of the auto-focusing light beam is approximately in the range of 405–465 nanometers.

26. A microscope optical inspection system as recited in claim 25 wherein each layered formation of multiple anti-reflective coatings is configured to transmit light wavelengths in the range of 247–370 nanometers.

27. A microscope optical inspection system as recited in claim 25 wherein the operational bandwidth of light includes light wavelengths in the range of approximately 190–450 nanometers, or portions thereof.

28. A microscope optical inspection system as recited in claim 25 wherein the auto-focusing light source is made of a composition selected from the group consisting of gallium-nitride, aluminum-gallium-nitride, and indium-gallium-nitride.

29. A microscope optical inspection system as recited in claim 25 wherein at least one of the anti-reflective coatings is formed of a material selected from the group consisting of $Sc_2O_3$, $HfO_2$, $ZrO_2$, and $Y_2O_3$.

30. A microscope optical inspection system as recited in claim 29 wherein an anti-reflective coating within a respective layered formation of anti-reflective coatings has a thickness in the range of approximately 25–250 nanometers.

31. A microscope optical inspection system as recited in claim 25 wherein the at least one optical lens element is part of an objective lens unit.

32. A microscope optical inspection system as recited in claim 25 wherein the optical inspection system is a cata-dioptric optical inspection system.

* * * * *

UNITED STATES PATENT AND TRADEMARK OFFICE
CERTIFICATE OF CORRECTION

PATENT NO. : 6,661,580 B1
DATED : December 9, 2003
INVENTOR(S) : Richard William Solarz It is certified that error appears in the above-identified patent and that said Letters Patent is hereby corrected as shown below:

<u>Column 1,</u>
Line 16, add the following new paragraph:
-- The U.S. Government has a paid-up license in this invention and the right in limited circumstances to require the patent owner to license others on reasonable terms as provided for by the terms of Cooperative Agreement Number 70NANB0H3038 awarded by NIST ATP. --

Signed and Sealed this

Twelfth Day of April, 2005

JON W. DUDAS
*Director of the United States Patent and Trademark Office*